(12) United States Patent
Siewerdsen et al.

(10) Patent No.: US 9,826,953 B2
(45) Date of Patent: Nov. 28, 2017

(54) INTEGRATION OF QUANTITATIVE CALIBRATION SYSTEMS IN COMPUTED TOMOGRAPHY SCANNERS

(71) Applicant: The Johns Hopkins University, Baltimore, MD (US)

(72) Inventors: Jeffrey H. Siewerdsen, Baltimore, MD (US); Abdullah Al Muhit, Baltimore, MD (US); John Carrino, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 144 days.

(21) Appl. No.: 14/405,759

(22) PCT Filed: Jun. 7, 2013

(86) PCT No.: PCT/US2013/044673
§ 371 (c)(1),
(2) Date: Dec. 4, 2014

(87) PCT Pub. No.: WO2013/185011
PCT Pub. Date: Dec. 12, 2013

(65) Prior Publication Data
US 2015/0173703 A1  Jun. 25, 2015

Related U.S. Application Data

(60) Provisional application No. 61/656,775, filed on Jun. 7, 2012.

(51) Int. Cl.
*A61B 6/00* (2006.01)
*A61B 6/03* (2006.01)

(52) U.S. Cl.
CPC .............. *A61B 6/583* (2013.01); *A61B 6/032* (2013.01); *A61B 6/505* (2013.01); *A61B 6/5217* (2013.01); *A61B 6/4085* (2013.01); *A61B 6/508* (2013.01)

(58) Field of Classification Search
CPC ....................................................... A61B 6/583
See application file for complete search history.

(56) References Cited

U.S. PATENT DOCUMENTS 7,056,021 B2   6/2006 Tsujii
2002/0186819 A1  12/2002 Proksa
(Continued)

FOREIGN PATENT DOCUMENTS

CN   1331571 A    1/2002
CN   101848678 A  9/2010

OTHER PUBLICATIONS

International Search Report of PCT/US2013/044673.

*Primary Examiner* — Dani Fox
(74) *Attorney, Agent, or Firm* — Venable LLP; Henry J. Daley; Miguel A. Lopez

(57) ABSTRACT

An embodiment in accordance with the present invention provides a device and method for a quantitatively calibrated computed tomography scanner. The device includes a gantry configured for receiving a patient or part of a patient. The gantry includes an X-ray source and a detector positioned opposite said X-ray source, such that said detector receives the X-rays emitted from the X-ray source. Calibration phantoms are integrated with the gantry and/or a device within the scanner so as to allow for calibration in quantitative CT measurements of Hounsfield units and/or bone mineral density.

20 Claims, 17 Drawing Sheets

(56) References Cited

U.S. PATENT DOCUMENTS

| | | | |
|---|---|---|---|
| 2004/0017936 A1* | 1/2004 | Gopinath | G06T 7/0012 382/131 |
| 2007/0086564 A1 | 4/2007 | Bruder et al. | |
| 2010/0266190 A1* | 10/2010 | Zagorchev | A61B 6/035 382/132 |
| 2011/0213242 A1 | 9/2011 | Budoff et al. | |

* cited by examiner

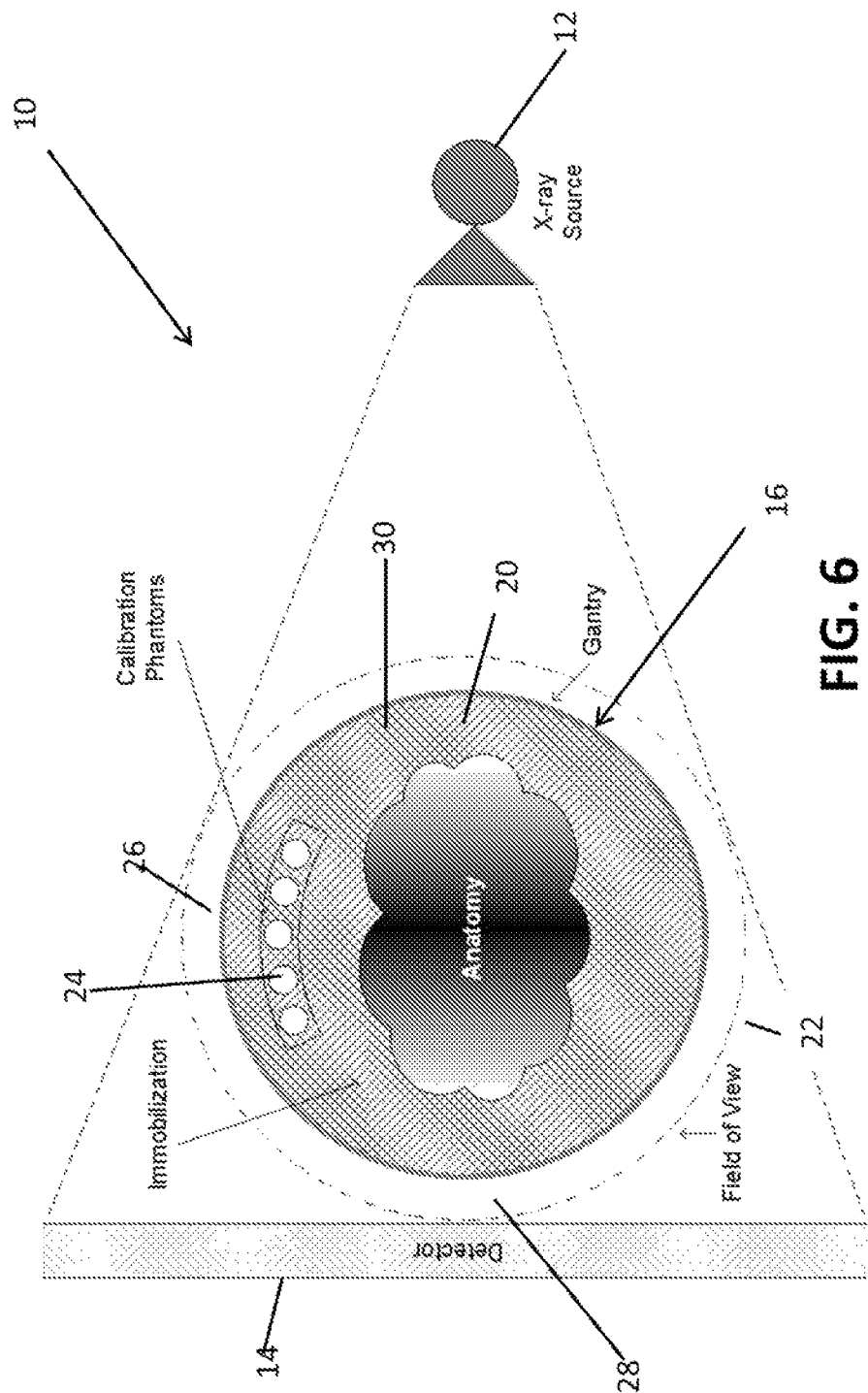

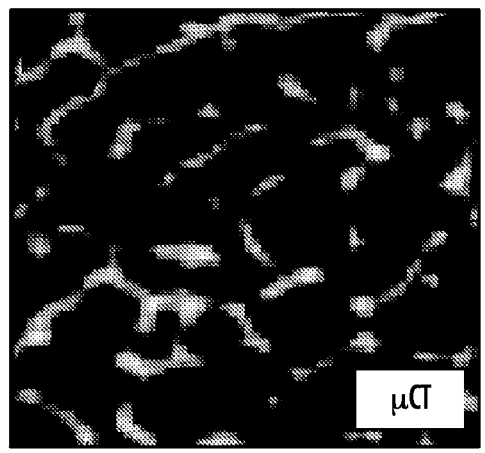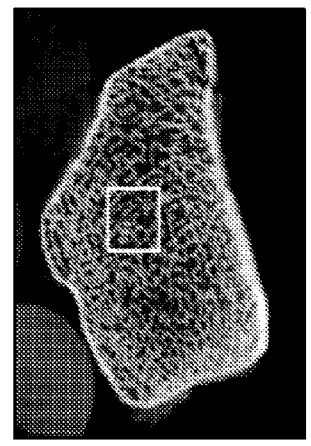
FIG. 12A
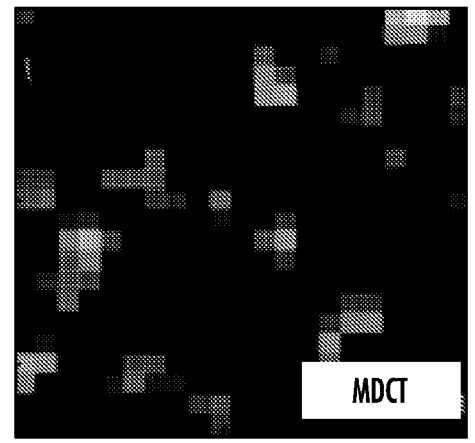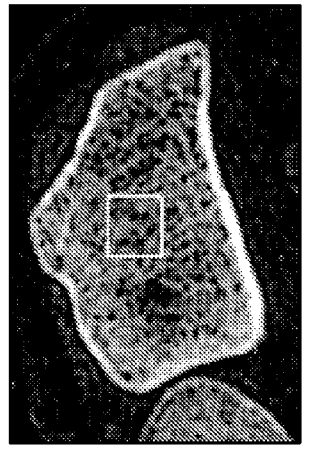
FIG. 12B
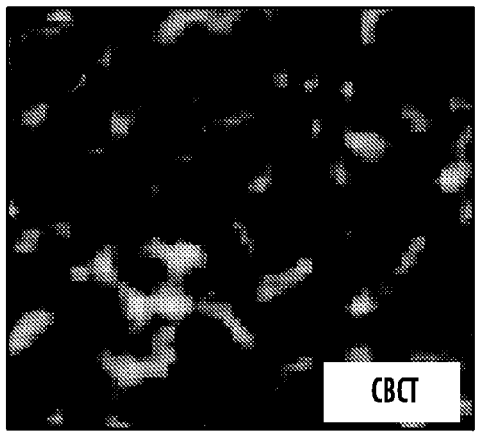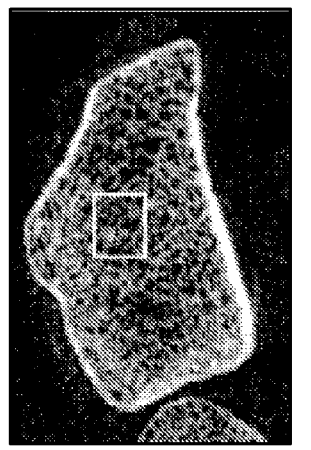
FIG. 12C

INTEGRATION OF QUANTITATIVE CALIBRATION SYSTEMS IN COMPUTED TOMOGRAPHY SCANNERS

CROSS REFERENCE TO RELATED APPLICATIONS

This is a national stage application under 35 U.S.C. §371 of PCT/US2013/044673 filed Jun. 7, 2013, the entire contents of which are incorporated herein by reference and this application claims the benefit of U.S. Provisional Application No. 61/656,775 filed on Jun. 7, 2012, which is incorporated by reference, herein, in its entirety.

FIELD OF THE INVENTION

The present invention relates generally to medical imaging. More particularly, the present invention relates to a device for determining bone mineral density in computed tomography (CT).

BACKGROUND OF THE INVENTION

Diagnosis and treatment of a spectrum of musculoskeletal diseases stand to benefit from high-quality, accurate imaging and morphological assessment as provided by peripheral quantitative CT (pQCT). For example, osteoporosis presents a growing health burden involving reduction in bone density leading to fragility fractures. Similarly, and particularly in an aging and obese population, osteoarthritis (OA) is an increasingly common degenerative joint disease caused by biomechanical stressors and an attendant disregulated response characterized by cartilage loss, with concomitant new bone growth, subchondral bony cysts, and other morphologic changes. Rheumatoid arthritis (RA) and other forms of inflammatory arthritis are autoimmune diseases characterized by hypertrophic synovium, cartilage loss, bone erosion, and ten-don damage. Such pathologies across a spectrum of bone and joint disorders exhibit signatures in intra-articular morphology, bone density, and bone morphometry, and the ability to more accurately assess these structures quantitatively could provide a means of earlier detection and improved assessment of treatment response.

Bone mineral density (BMD) is commonly measured for characterization of osteoporosis using dual-energy x-ray absorptiometry (DEXA) or quantitative CT (QCT). Other image-based measures present additional, potentially more sensitive assessments of pathology, including bone volume fraction (BV/TV), trabecular thickness (Tb.Th), structure model index (SMI), degree of anisotropy (DA), and high-resolution characterization of the joint space morphology. Such metrics have been conventionally challenged because of the limited spatial resolution of clinical (whole-body) CT scanners and have therefore been less frequently utilized. However, these potential biomarkers offer important insight into different bone and joint-related disorders, disease progression and response.

For example, osteoporosis is a common metabolic bone disorder that causes bone fragility and consequent fractures. In the US alone, osteoporosis is responsible for about 1.5 million vertebral and non-vertebral (mainly hip and wrist) fractures each year. Early detection and quantitative assessment of osteoporosis and fracture risk, predominantly depends on bone mineral density (BMD) measurements. Dual-Energy X-ray Absorptiometry (DXA) can be used to provide BMD measurements. However it is only able to measure areal densities.

Quantitative Computed Tomography (QCT), on the other hand, can be used to calculate volumetric densities and provide significantly more accurate BMD measurements. Therefore, QCT is becoming a widely accepted method for BMD assessment. In QCT, some form of calibration or reference phantoms are imaged either before or during a patient scan at close proximity to the desired anatomy. The attenuation coefficients and known densities of the phantoms are then used to extrapolate the unknown density of the patients' bony structures. However, variability in phantom location can cause degradation in BMD accuracy, and positioning of the phantoms can affect overall workflow, total scan time, and patient comfort. Also, variability in phantom location requires user interaction in localizing them during BMD calculations and can affect the accuracy of BMD estimates. Traditional CT scanner designs do not directly incorporate any form of calibration phantoms; rather, phantoms are usually employed as an add-on component, typically laid on the scanner bed under the patient or applied in calibration tables generated before (or after) the imaging exam. As a result, densitometry information can only be derived from the CT scan if an additional calibration phantom is introduced at the time of the scan or, perhaps, if a separate scan is required for quantitative imaging purposes.

It would therefore be advantageous to provide a new system and method for integrating the reference calibration system directly into the scanner and gantry enclosure, such that the phantoms are always at a predetermined location within the scanner geometry and field-of-view (FOV). The reference phantoms will therefore be present during each scan, and there is no need for add-on devices or repositioning the phantoms for each scan. Direct integration of the calibration system with the CT scanner is expected to improve the accuracy of BMD measurement and improve clinical workflow.

SUMMARY OF THE INVENTION

The foregoing needs are met, to a great extent, by the present invention, wherein in one aspect a device for calibrated computed tomography (CT) scanning including a gantry. The gantry defines a generally cylindrical opening configured for receiving a patient or part of a patient for examination and also has an inner wall of the gantry defining an interior space configured for housing components of the scanner. An X-ray source is configured to emit X-rays that penetrate the patient or part of a patient. The X-ray source and detector can be housed within the gantry, with the detector positioned opposite the X-ray source, such that said detector receives the X-rays emitted from the X-ray source. The detector also defines a nominal field of view for the device, such that any item in the field of view is imaged by the device. Calibration phantoms are integrated directly within the scanner gantry such that X-rays traverse elements of the calibration phantom in some or all X-ray projections acquired during the scan. Whether the calibration phantoms are within or outside the nominal field of view, provided that they are within the X-ray beam for some or all X-ray projections delivered during the scan, then the calibration phantoms may be imaged in each scan and used directly in calibration for BMD measurement. An exemplary embodiment involves a scanner for which the inner wall of the gantry is within the X-ray field of view and within which a calibration phantom is integrated such that an image of the phantom may be obtained simultaneous with the patient scan.

In accordance with another aspect of the present invention, the calibration phantoms are integrated with the scanner within the opening configured to receive the patient (or part of the patient) defined by the gantry. The calibration phantoms can therefore be positioned in the interior space defined by the inner wall of the gantry, within the inner wall of the gantry, or adjacent to the patient. The device containing the calibration phantoms can include, for example, an encasement used in association with the patient for positioning or immobilization. An exemplary embodiment of the calibration phantom includes approximately five calibration phantoms, which can be generally cylindrical in shape. The calibration phantoms are of known dimensions and can cover part of or the entire length of the field of view of the scanner, and can have a solid composition. The calibration phantom has a known Hounsfield unit (HU) and a known calcium density. The device is further configured for weight bearing imaging.

In accordance with another aspect of the present invention, a device for calibrated cone beam computed tomography (CBCT) scanning includes a gantry. The gantry defines a generally cylindrical opening configured for receiving the patient for examination. The gantry also has a wall configured for housing components of the device. The device also includes an X-ray source configured to emit X-rays that penetrate the patient and a detector positioned opposite said X-ray source. The detector receives the X-rays emitted from the X-ray source, and the detector defines a nominal X-ray field of view for the device such that any item in the field of view is imaged by the device. A calibration phantom is positioned around the generally cylindrical opening, such that the calibration phantom is imaged by the device.

In accordance with still another aspect of the present invention, the calibration phantom takes the form of approximately six calibration phantoms. The approximately six calibration phantoms are positioned longitudinally in a ring around the generally cylindrical opening. Additionally, the approximately six calibration phantoms are spaced such that they are all at least partially within the field-of-view.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIG. 6 illustrates an axial view of a scanner having phantoms integrated on a device internal to the wall of the gantry in association with a patient positioning or immobilization device according to an embodiment of the invention.

FIGS. 12A-12G illustrate image and graphical views of a mophometry analysis in a cadaveric radius using CBCT, μCT, and MDCT.

DETAILED DESCRIPTION

Figure 1:
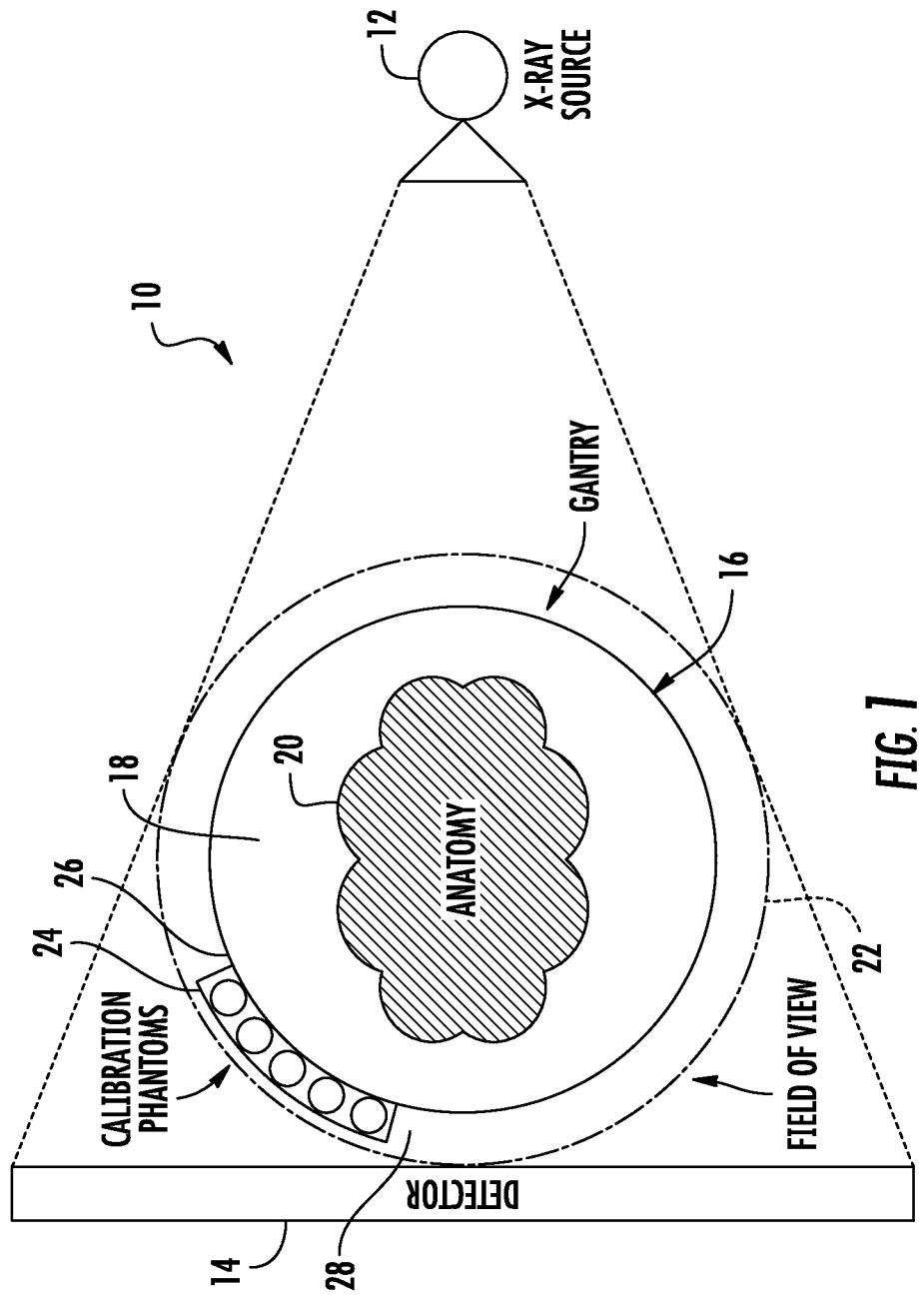
FIG. 1 illustrates an axial view of a scanner having phantoms integrated into the scanner enclosure according to an embodiment of the invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a device and method for a quantitatively calibrated computed tomography scanner. The device includes a gantry configured for receiving a patient, part of a patient, or a patient's extremity. The gantry also has an enclosure configured for housing additional components of the device. An X-ray source can be positioned within the interior space of the gantry or in any other suitable position known to one of skill in the art. A detector can also be housed within the interior space of the gantry and is positioned opposite said X-ray source, such that said detector receives the X-rays emitted from the X-ray source. Alternately, the detector can also be positioned in any other suitable position known to one of skill in the art. The detector defines a nominal field of view for the device, and anything in the nominal field of view is imaged by the device. Objects outside the field of view can be similarly imaged but may involve more sophisticated image reconstruction techniques (several established in prior art) to form accurate computed tomography images. Calibration phantoms are positioned within or outside the nominal field of view. The calibration phantoms are imaged by the device to allow for calibration.

As illustrated in FIGS. 1-6 a CT scanner 10 is comprised of an X-ray source 12 and detector a 14, which are both shown as housed in a gantry 16. Alternately, the X-Ray source 12 and the detector 14 can be placed in any other suitable position known to one of skill in the art. The gantry 16 usually defines a cylindrical opening 18, between the X-ray source 12 and detector 14, for examination of a portion of the anatomy 20 of the patient. While FIGS. 1-6 illustrate the examination of just a portion of the patient's anatomy, it is well known to those skilled in the art that CT scanners can be used to examine not only specific portions of a patient's anatomy, but also whole regions of the patient or the patient's entire body. Therefore, the illustration of the portion of the patient's anatomy is included merely as an example, and is not intended to be considered limiting. The X-ray source 12 emits X-rays that penetrate the anatomy 20, and the attenuated X-ray values are recorded by the detector 16 as projection images. The X-ray source 12 and detector 14 rotate around the opening 18 in the gantry 16 or patient anatomy 20 and capture a number of projection images in order to reconstruct cross-sectional (axial) images of the anatomy 20.

An embodiment of the invention involves a scanner 10 taking the form of an extremity cone-beam CT scanner configuration (with flat-panel detector), as shown in FIG. 1. Although an extremity cone-beam CT scanner is illustrated in FIG. 1, this is simply an example, and is not intended to limit the type of CT scanner used or the anatomy examined. The nominal field-of-view (FOV) 22 of the same scanner is shown by a dotted circle. It is worth noting that FOV 22 may differ due to different configurations. In this particular configuration, illustrated in FIG. 1, the FOV 22 extends beyond the anatomy 20 and contains part of the gantry 16. Hence, calibration phantoms 24 can be integrated on a wall 26 of the gantry 16 in a space 28 between the opening 18 of the gantry 16 and detector 14. This ensures that the phantoms 24 are always within the FOV 22 of the scanner 10. Therefore, reconstructed cross-sectional images taken with the scanner 10 will contain cross-sections of calibration phantoms 24. The cross-sections of the phantoms 24 can be used as reference to measure/extrapolate BMD of desired structures. However, it should be noted that the cross-sections of the phantoms 24 in the resultant images could be used to assess any number of conditions known to one of skill in the art.

Figure 2:
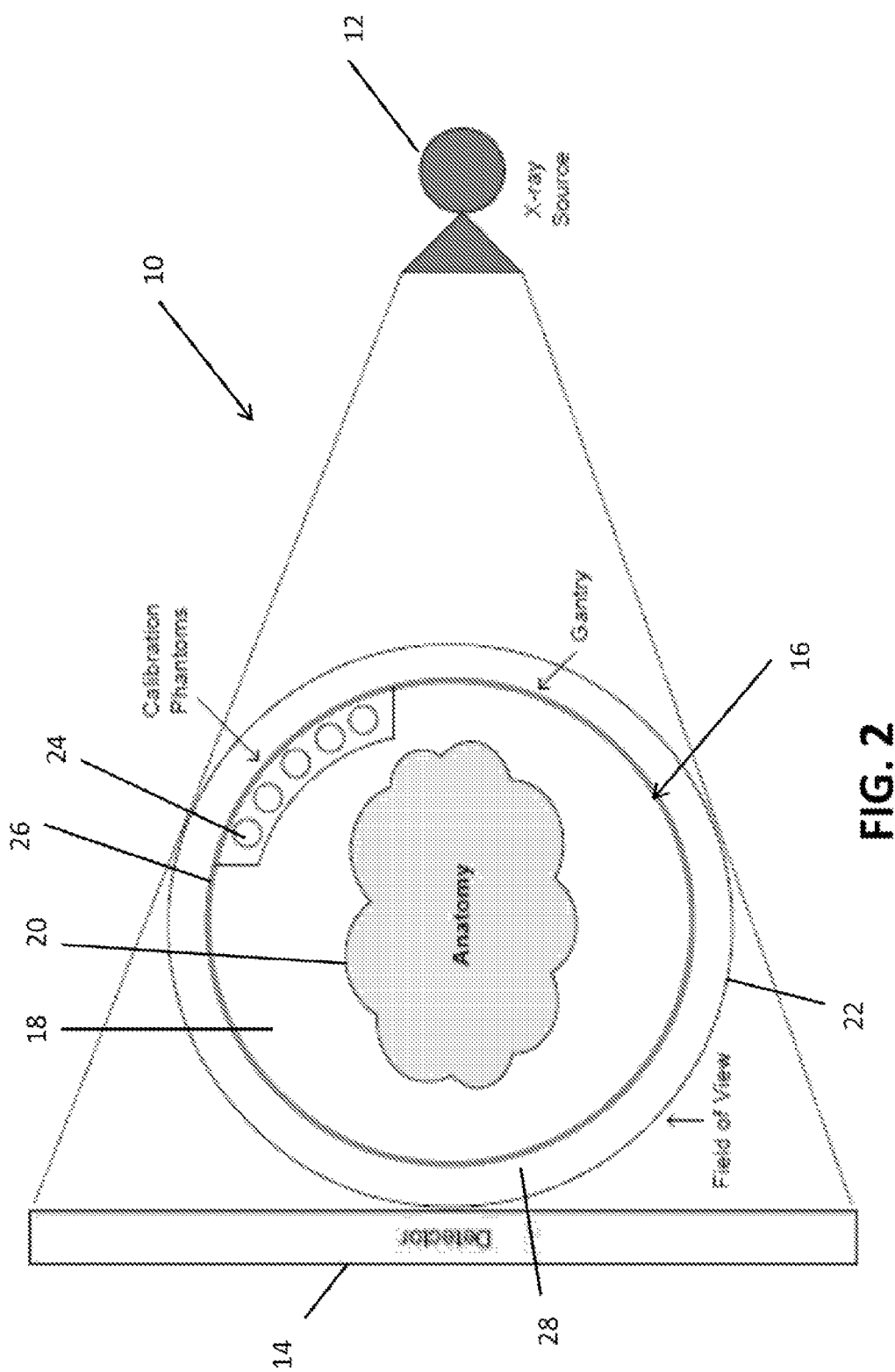
FIG. 2 illustrates an axial view of a scanner having phantoms integrated on an internal wall of the gantry according to an embodiment of the invention.
Figure 3:
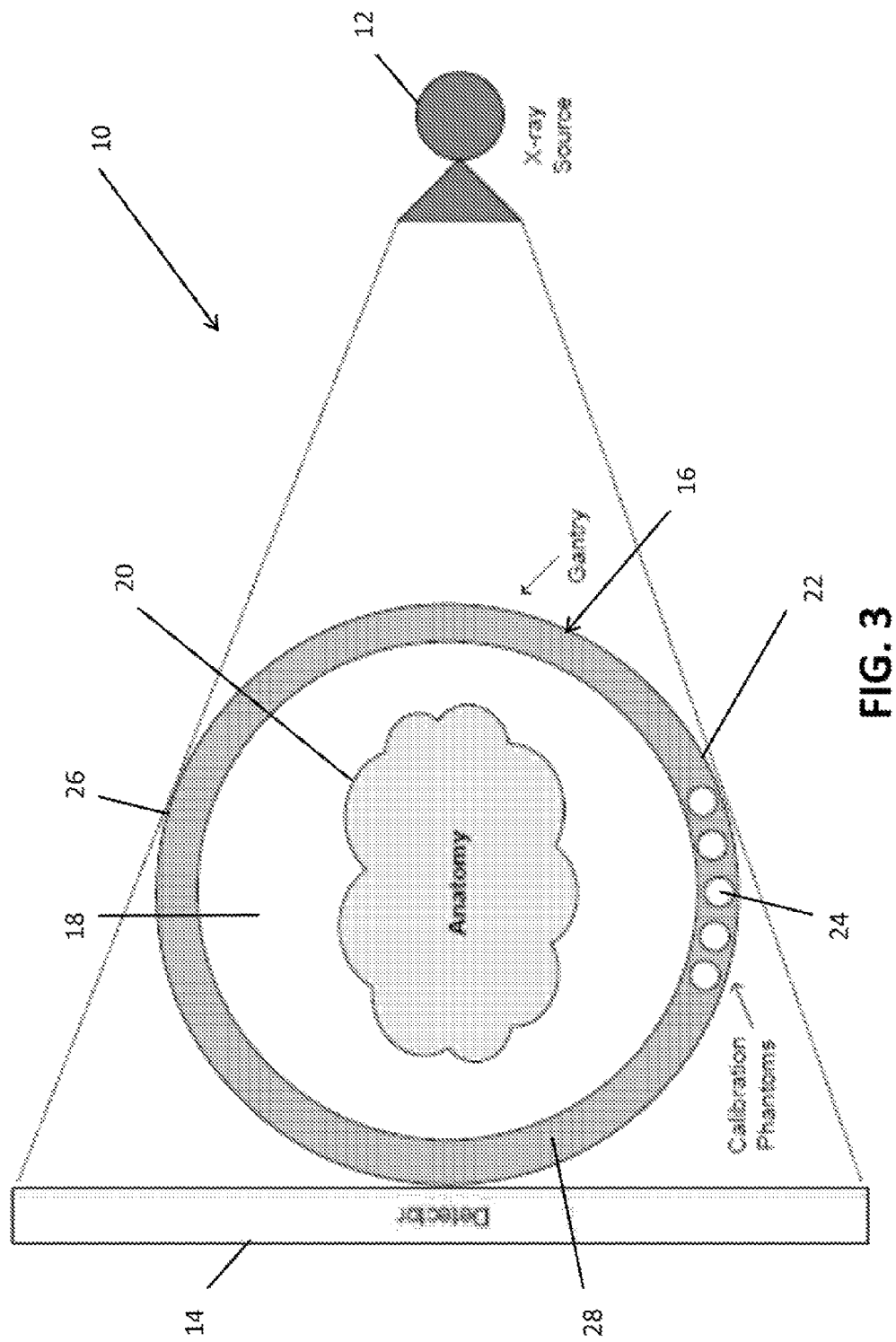
FIG. 3 illustrates an axial view of a scanner having phantoms integrated into the wall of the gantry according to an embodiment of the invention.
Figure 4:
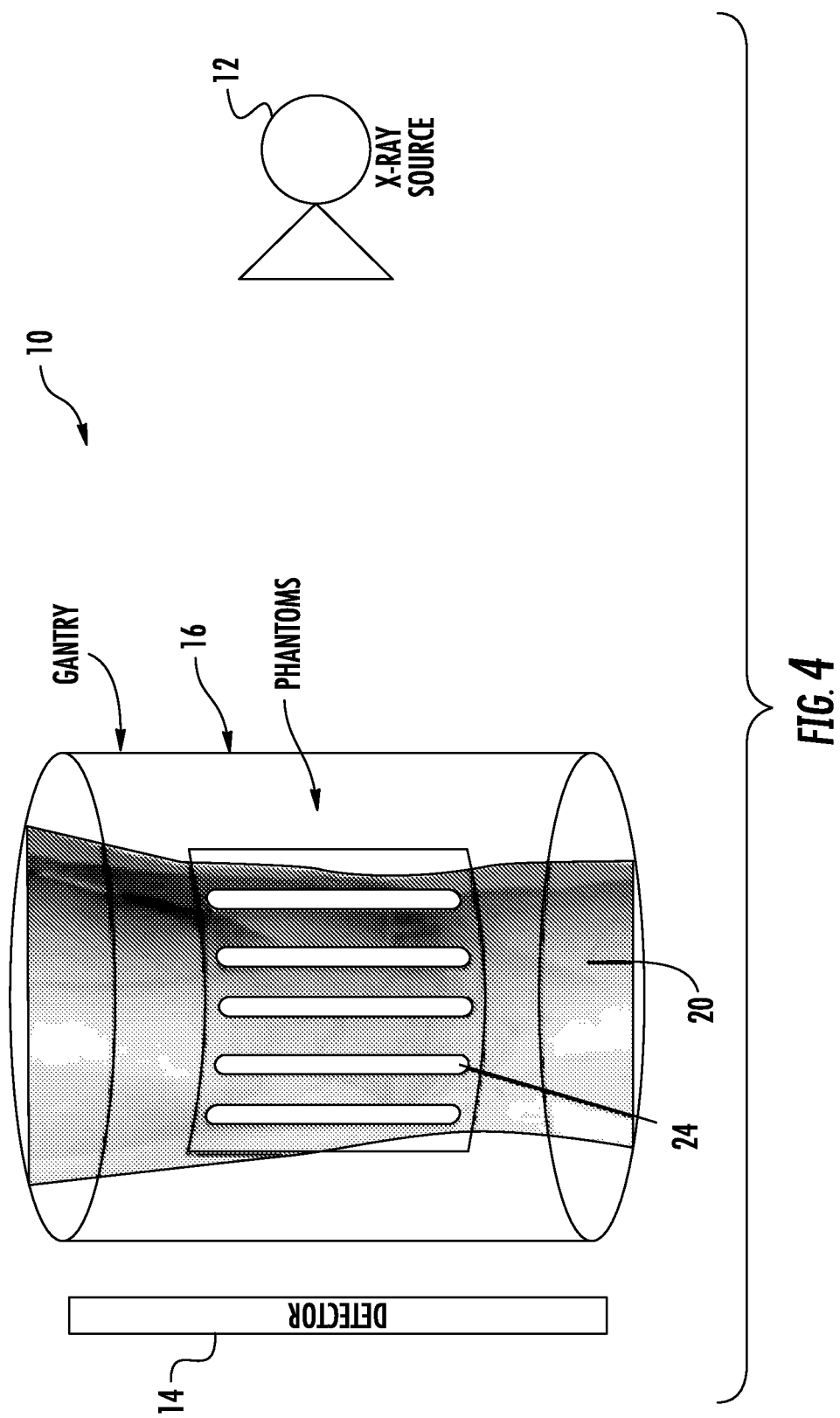
FIG. 4 illustrates a side view of a possible embodiment of the present invention wherein the calibration phantom is integrated within the gantry of the scanner.

FIGS. 2 and 3 illustrate alternate ways to position the calibration phantoms 24. In these configurations, the phantoms 24 are attached within the gantry opening 18 or patient examination space (FIG. 2) or integrated within the gantry wall (FIG. 3). A side view of the same concept is shown in FIG. 4, where a human knee 20 is demonstrated to be inside the opening 18 in the gantry 16 of the scanner 10 for imaging purposes.

Figure 5:
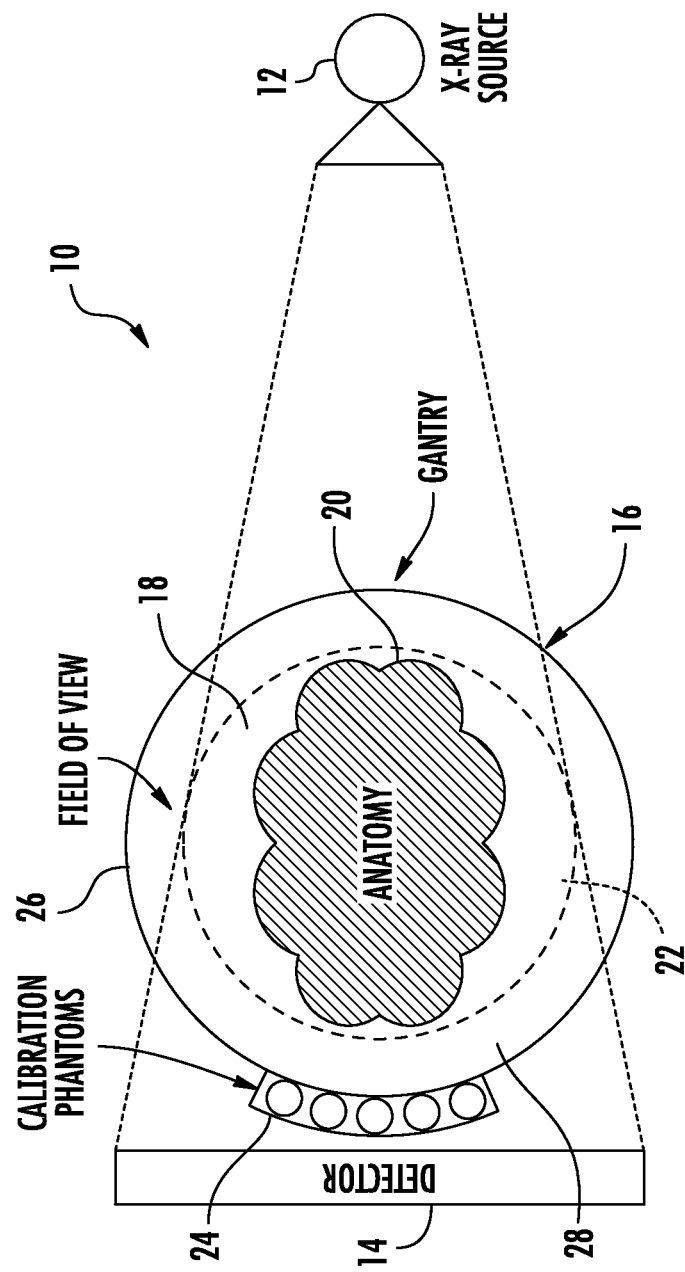
FIG. 5 illustrates an axial view of an alternative embodiment of the scanner for which the calibration phantoms are outside the nominal X-ray field of view.

FIG. 5 demonstrates another alternative configuration of proposed system where calibration phantoms 24 are integrated with the scanner 10, but are outside the nominal reconstruction field of view 22 and therefore, not fully sampled. Although the phantoms 24 are under-sampled in this scenario, measurement of the calibration phantom can still be accomplished by means of reconstruction extending beyond the nominal field of view 22, including methods in which prior/known information can be used to reconstruct them accurately known to those of skill in the art. This enables quantitative imaging when the phantoms are placed somewhere in between the source and the detector, but not always in the nominal field of view.

FIG. 6 illustrates an additional configuration of the proposed system further including an immobilization device 30 positioned adjacent to the patient anatomy 20. The immobilization device 30 can be formed from an inflatable bladder, foam, or any other suitable material known to one of skill in the art. Further, the immobilization device 30 can be configured to immobilize a portion of anatomy, a region, or the whole of the patient. In the example illustrated in FIG. 6, the immobilization device 30 takes the form of an air bag, configured to immobilize a patient's knee. As illustrated in FIG. 6, the calibration phantoms 24 are integrated within the immobilization device 30.

An embodiment of the proposed system involves cylindrical phantom inserts of solid composition, although any phantom known to one of skilled in the art could also be used. As shown in FIG. 4, the inserts/phantoms 24 may be long enough to cover the entire FOV 22 of the scanner 10, so that all reconstructed cross-sectional images contain a cross-section of the phantoms 24. The phantoms are expected to present known densities that provide the basis for quantitative calibration of the patient image. A total of five phantom inserts are shown in FIGS. 1-6, although any suitable number of phantoms conceived by one of skilled in the art could be used. In the case of FIGS. 1 and 2, the solid encasement that holds the phantoms 24 may have uniform density that is different from the reference phantoms 24. This also applies to FIG. 3, where the wall 26 of the gantry 16 may have uniform density but one that is dissimilar to the density of the phantoms. Alternately, the phantoms do not have to be entirely captured within the FOV, as illustrated in and described with respect to FIG. 5.

The reference phantoms may be integrated at a predefined/fixed location, whether that is within or attached to the structure of the CT scanner or whether that is within or within an object not permanently coupled to the CT scanner, such as an immobilization device, as described with respect to FIG. 6. This eliminates the need to re-position the phantoms during each scan. This is beneficial from a workflow and time management perspective. The concept also eliminates the need to place the reference phantoms in close proximity to patients. This is an improved solution in comparison to previous methods, where the phantoms are placed underneath or over the patient or surrounding an extremity of the patient, which might cause discomfort. A conventional CT scanner does not contain calibration/reference systems in order to infer quantitative information of the resulting scan. Hence, patients might need to undergo a separate scan together with add-on phantoms for quantitative purposes, which may add radiation exposure, time, and cost. The proposed method and device eliminates the need to perform a separate scan and provides all information for quantitative imaging in each scan. Hence, quantitative information can be derived from any scan.

Exemplary Embodiments and Uses

Exemplary implementations of the present invention are described herein, in order to further illustrate the present invention. The exemplary implementations are included merely as an example and are not meant to be considered limiting. Any implementation of the present invention on any suitable subject known to or conceivable by one of skill in the art could also be used, and is considered within the scope of this application.

Figure 7B:
FIGS. 7A and 7B illustrated side and perspective views of a dedicated CBCT scanner for extremity imaging according to an embodiment of the present invention.
Figure 7A:

A cone-beam CT (CBCT) system specifically for musculoskeletal imaging, according to an embodiment of the present invention is illustrated in FIG. 7. The CBCT system, according to the present invention, provides superior spatial resolution in comparison to MDCT, opening the possibility for pQCT on such dedicated systems. Compared to extremity micro-CT (for example, XTreme™ CT, ScanCo, Switzerland) such CBCT scanners provide a large field of view (~22 cm) and spatial resolution and soft-tissue contrast resolution comparable or superior to MDCT. The system also allows imaging of weight-bearing lower extremities as well as multi-mode planar (radiography), kinematic (fluoroscopy), and 3D volumetric (CBCT) imaging on the same platform.

Initial technical assessment of the CBCT scanner according to the present invention, demonstrate sub-mm (~0.5 mm) isotropic spatial resolution, providing superior visualization of trabecular and cortical bone details compared to MDCT at low dose (~10 mGy; ~0.1 mSv to the distal extremities). Initial patient studies suggest that soft-tissue contrast resolution is satisfactory for visualization of ligaments, tendons, and cartilage at a level comparable to state-of-the-art MDCT, though soft-tissue contrast resolution remains an area of ongoing improvement in artifact correction techniques and novel image reconstruction methods. The compact design of the system allows a 22×22×22 $cm^3$ field of view (FOV) for scanning the hand, wrist, elbow, knee, foot, and ankle. The present invention allows a clinician to derive pQCT analysis directly from CBCT images acquired with each scan, potentially eliminating the need for a separate DEXA or pQCT examination. Such quantitative imaging capability offers an advance to diagnosis, staging, and treatment response assessment in osteoporosis, osteoarthritis, rheumatoid arthritis, and trauma.

Assessment of Bone Mineral Density (BMD)

Figure 8B:
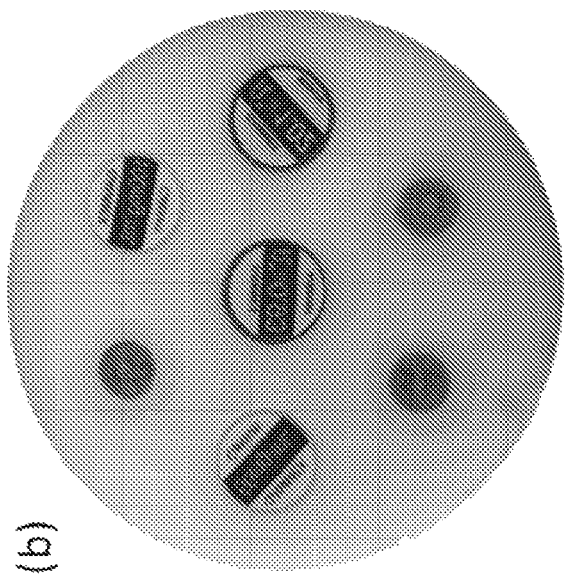
FIG. 8B illustrates a polyethylene phantom with known bone mineral density inserts, according to an embodiment of the present invention.
Figure 8A:
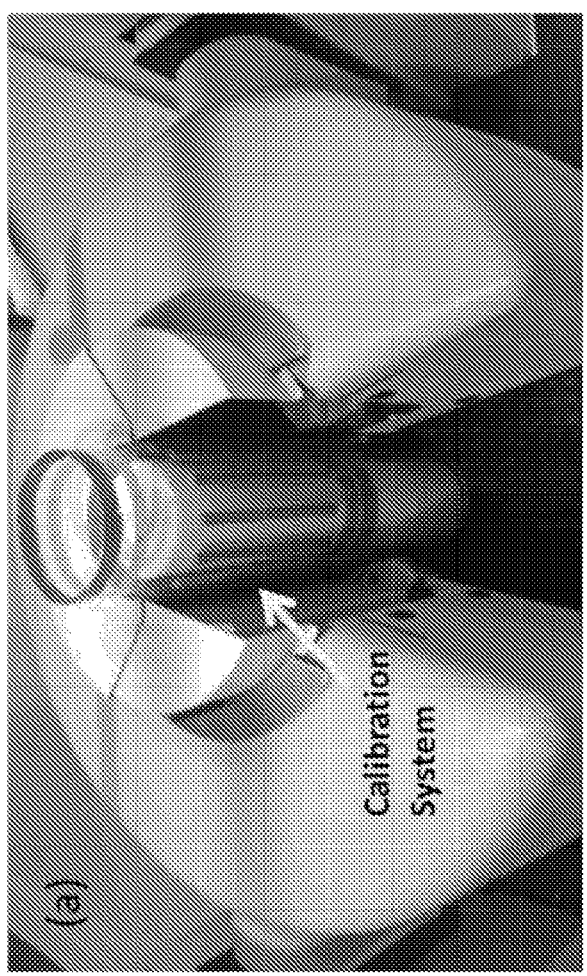
FIG. 8A illustrates a calibration system integrated with the scanner door or gantry for bone mineral density estimation, according to an embodiment of the present invention.
Figure 9D:
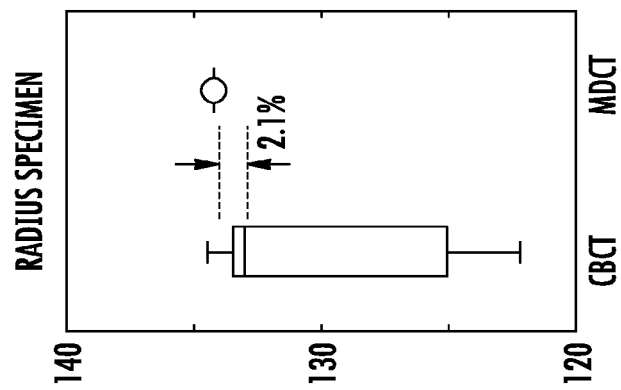
FIGS. 9A-9D illustrate BMD measurements using the CBCT scanner in comparison to MDCT.
Figure 9C:
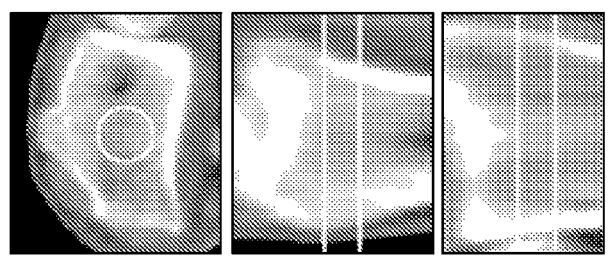
Figure 9B:
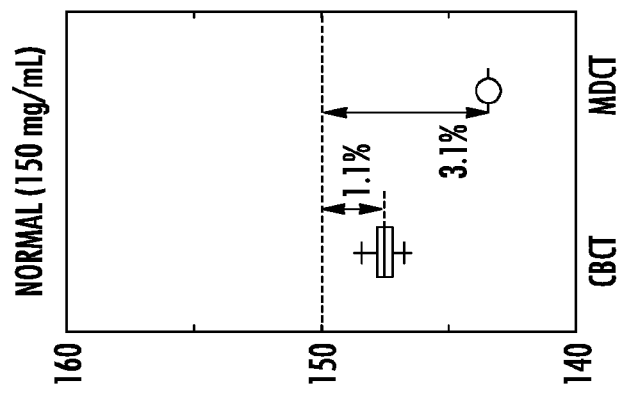
Figure 9A:
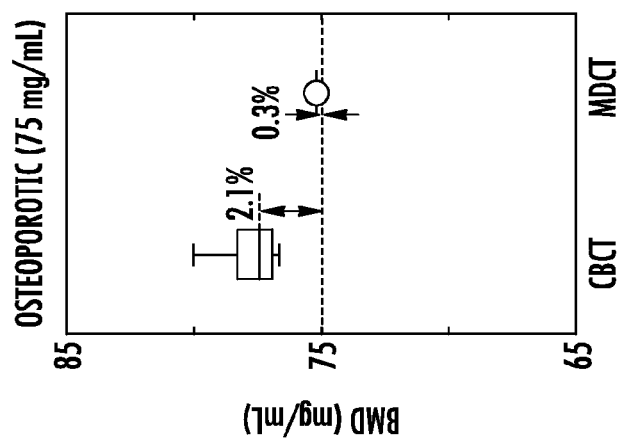
Figure 10C:
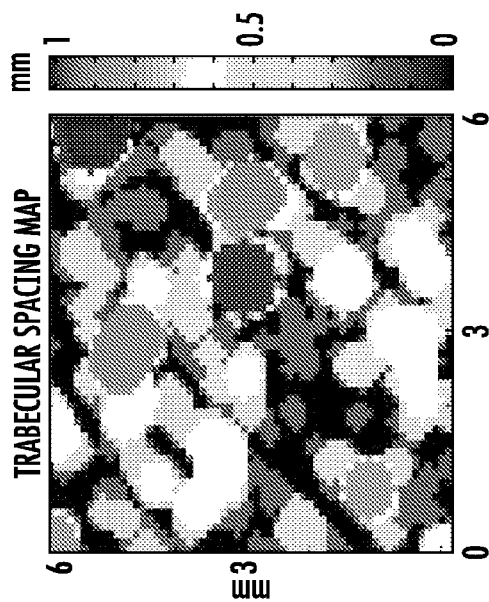
FIGS. 10A-10C illustrate an image and maps of an assessment of trabecular morphometry from a cadaveric radius using high resolution CBCT.
Figure 10B:
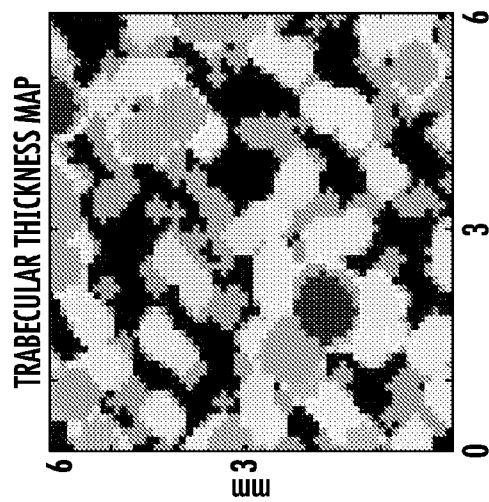
Figure 10A:
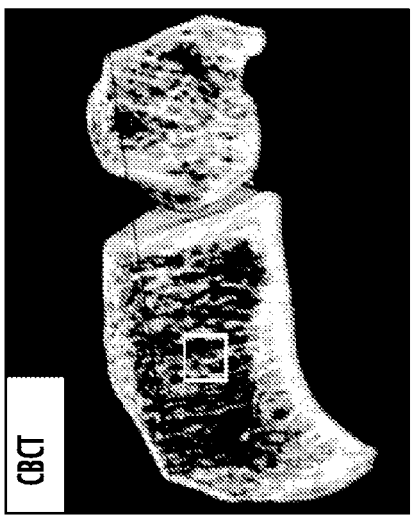
Figure 11A:
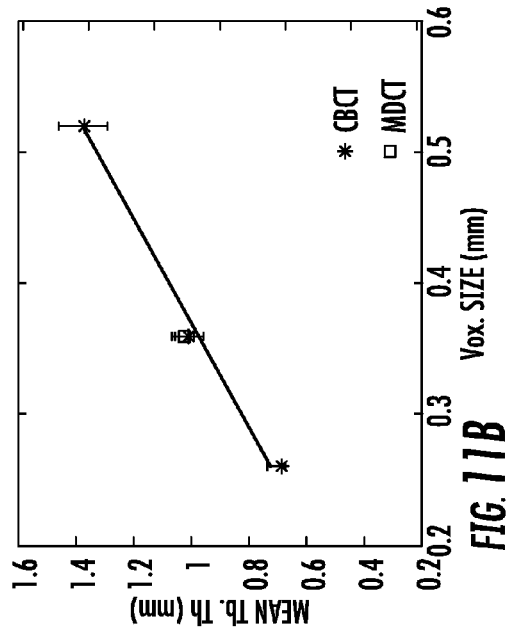
FIGS. 11A-11D illustrate a graphical view of an assessment of trabecular mophometry from a cadaveric radius using high resolution CBCT.
Figure 11B:
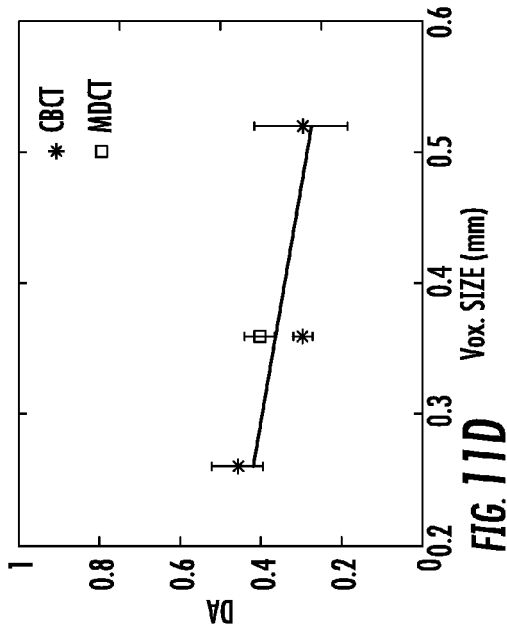
Figure 11C:
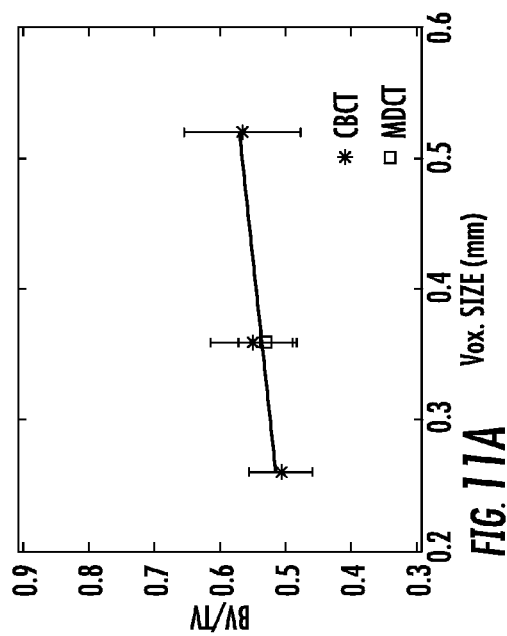
Figure 11D:
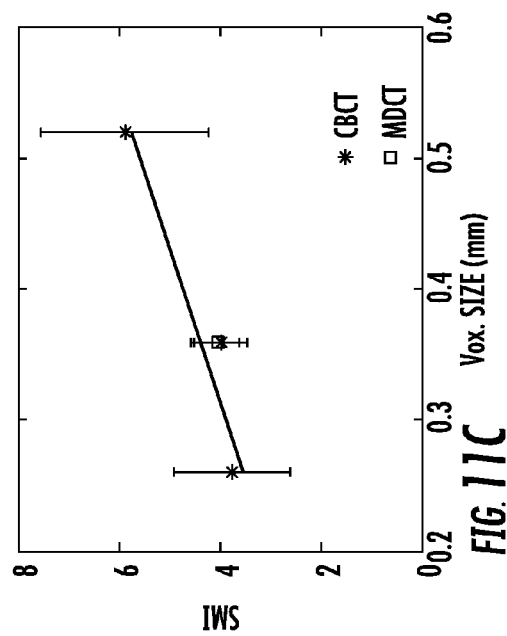
Figure 12D:
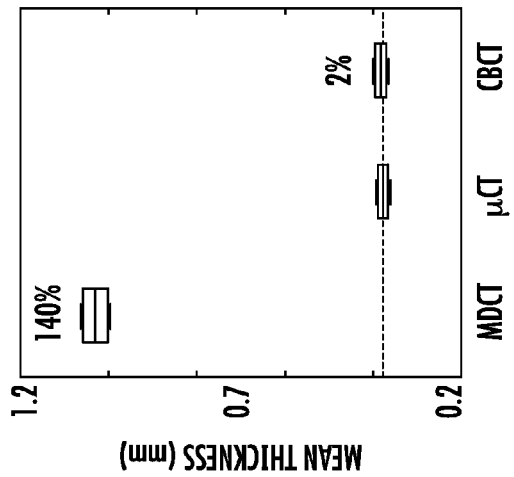
Figure 12E:
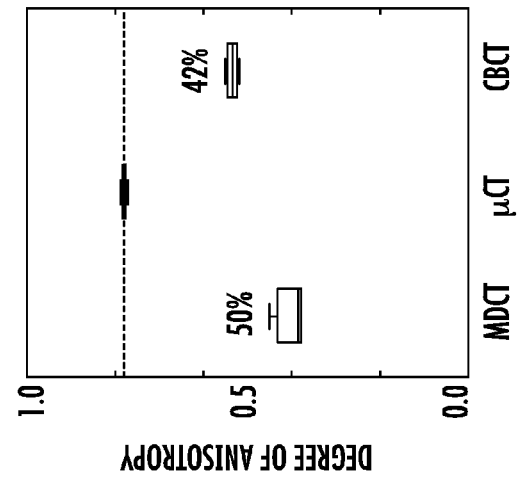
Figure 12F:
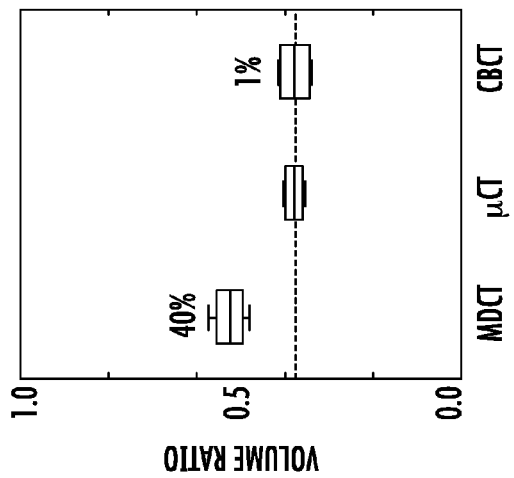
Figure 12G:
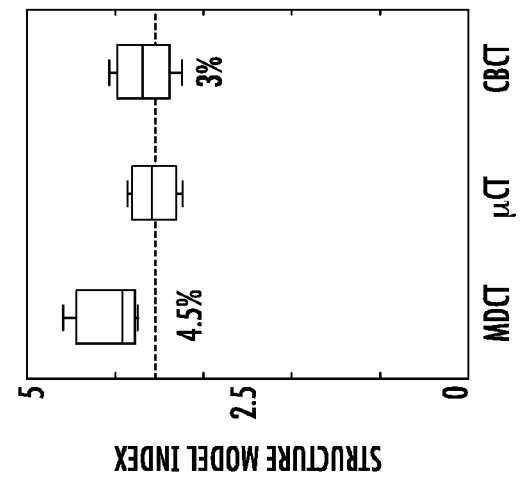
Figure 13D:
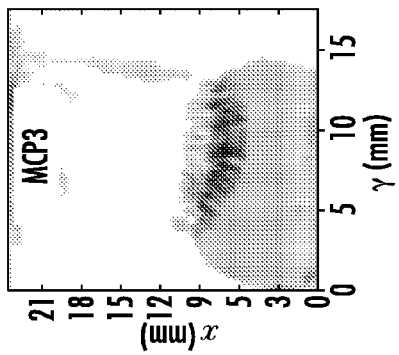
FIG. 13 illustrates a joint space width calculation using an electrostatic "capacitor" model in which field lines describe a unique, non-degenerate map of the intra-articular space.
Figure 13C:
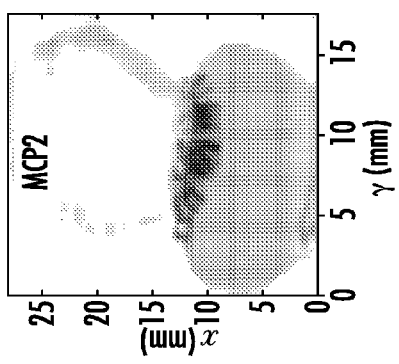
Figure 13F:
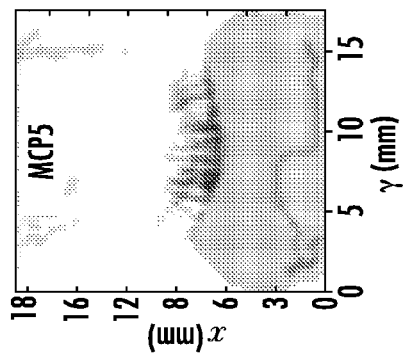
Figure 13B:
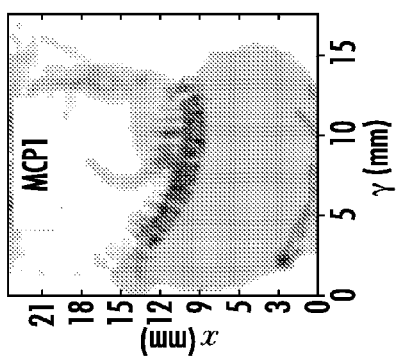
Figure 13E:
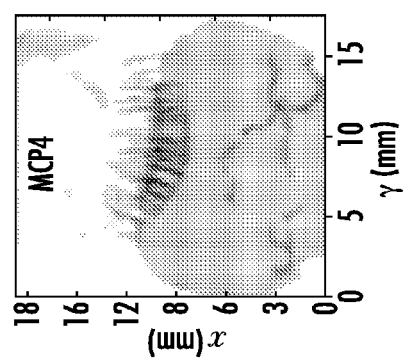
Figure 13A:
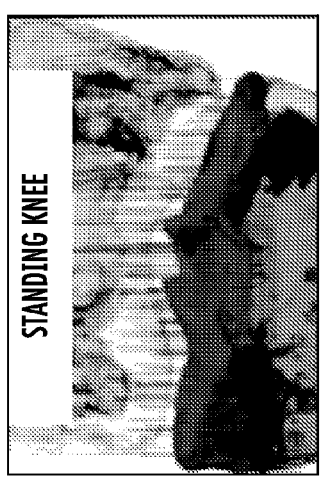
Figures 14A, 14B, 14C:
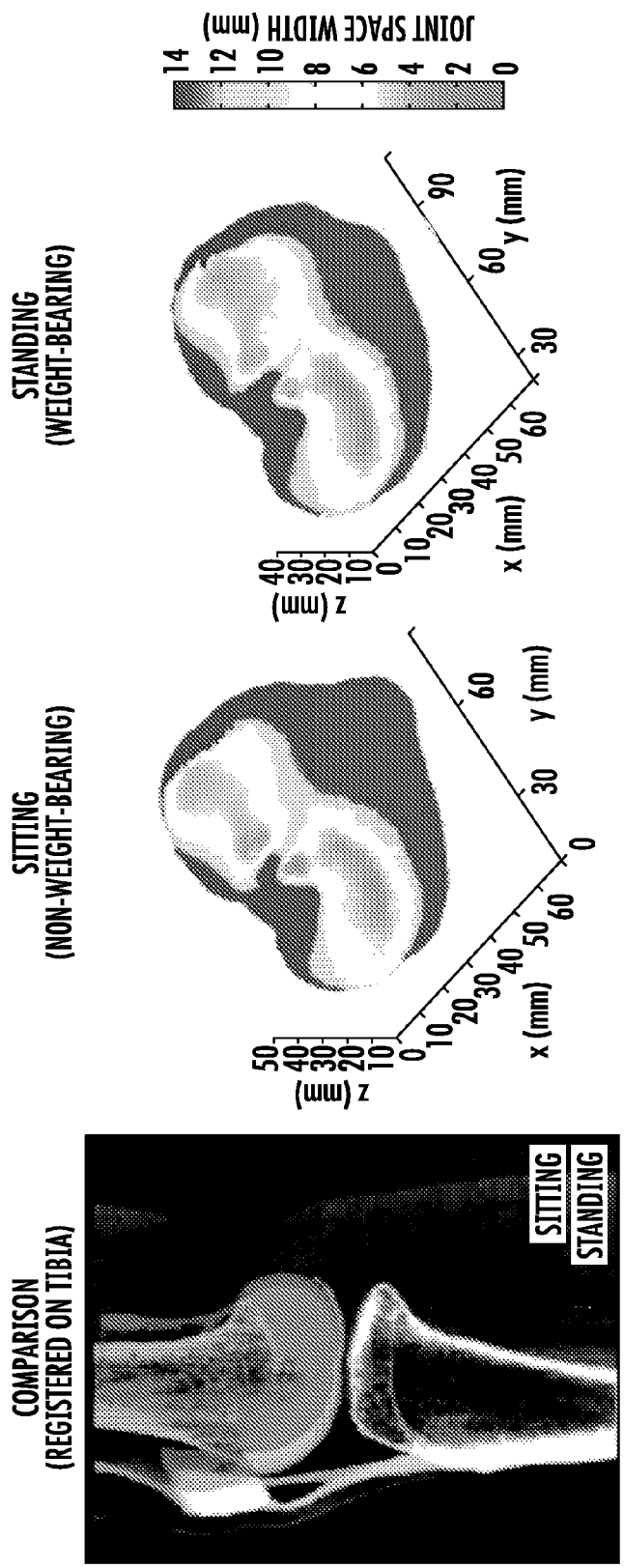
FIGS. 14A-14C illustrate image and graphical representations of joint space differences during sitting and standing.
Figures 15A, 15B, 15C, 15D:
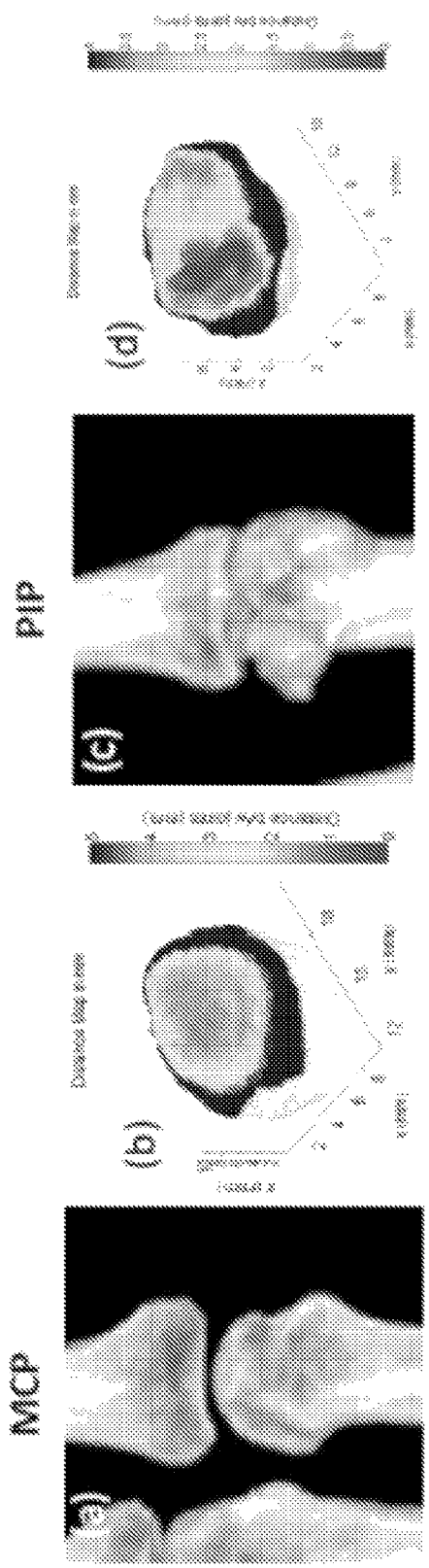
FIGS. 15A-15D illustrate and graphical representations of joint space differences during sitting and standing.

Measurement of bone mineral density (BMD) is important in the detection and staging of osteoporosis as well as assessment of fracture risk. To obtain BMD information automatically from each CBCT scan, a QCT calibration phantom is integrated directly in the scanner enclosure, illustrated in FIGS. 8A and 8B, providing automatic Hounsfield Unit (HU) calibration with every scan. The known HU values and calcium content of the phantoms allow automatic HU calibration and BMD measurement with each scan in a manner that accounts for variations arising from the size of the subject as well as spatial variation along the axial direction. The calibration phantom included six rods oriented longitudinally in a ring about the inner bore of the scanner, illustrated in FIGS. 8A and 8B, each presenting a known HU and calcium density. In addition to the correction provided by the calibration phantom, the results below incorporated a simple x-ray scatter correction (viz., subtraction of a constant scatter fluence estimate in projection data), with future work to include more sophisticated scatter correction methods. The accuracy in BMD measurements was assessed in a 16 cm diameter polyethylene cylinder incorporating inserts representing a range of calcium density, as illustrated in FIGS. 8A and 8B. As shown in FIGS. 9A-9D, the CBCT system provided BMD measurements typically within 3% of the true values (i.e. 75, 150 mg/mL CaHA), matching the accuracy of MDCT within ~2%. The present invention could also be used to implement a fast Monte Carlo scatter correction technique and an iterative beam-hardening correction.

Subchondral Bone Structure (Morphometry)

Changes in intra-osseous architecture represent an important component of the pathobiology of a spectrum of bone and joint disorders, including osteoporosis and osteoarthritis. Subchondral bone morphology metrics, such as bone volume fraction (BV/TV), trabecular thickness (Tb.Th), and trabecular spacing (Tb.Sp), characterize the quality of trabecular architecture. Similarly, the degree of anisotropy (DA) is a measure of isotropic nature/orientation of trabeculae within a volume (DA: 0=isotropic, 1=anisotropic), and the structure model index (SMI) describes the plate-like, rod-like, or sphere-like geometry of trabeculae (SMI: 0=plate-like, 3=rod-like, 4=sphere). These metrics were defined as follows:

$$\frac{BV}{VT} = \frac{\text{bone vol.}}{\text{total vol.}} \quad (1)$$

$$Tb \cdot Th = \frac{\sum d_n}{N} \quad (2)$$

where d is the diameter of the largest sphere that can be fitted within a trabecular structure at a point, and N is the total number of points. The SMI was given by:

$$SMI = 6 \times \left(\frac{s' \times v}{s^2}\right) \quad (3)$$

where is the change in surface area after voxel dilation, S is the original surface area, and V is the volume size. Finally, the DA was given by:

$$DA = 1 - \left(\frac{sx}{lx}\right) \quad (4)$$

where sx and lx refer to the short axis and long axis of an ellipsoid fit to the trabecular structures. Evaluation of such pQCT morphological metrics in CBCT images of a cadaveric knee and hand are shown in FIGS. 10A-10C, 11A-11D, and 12A-12G in comparison to micro-CT (taken as gold-standard) and clinical MDCT. The results demonstrate an improvement in accuracy for each metric assessed from CBCT in comparison to MDCT, with accuracy approaching that of micro-CT within ~5%.

Assessment of Joint Space

Figure 16:
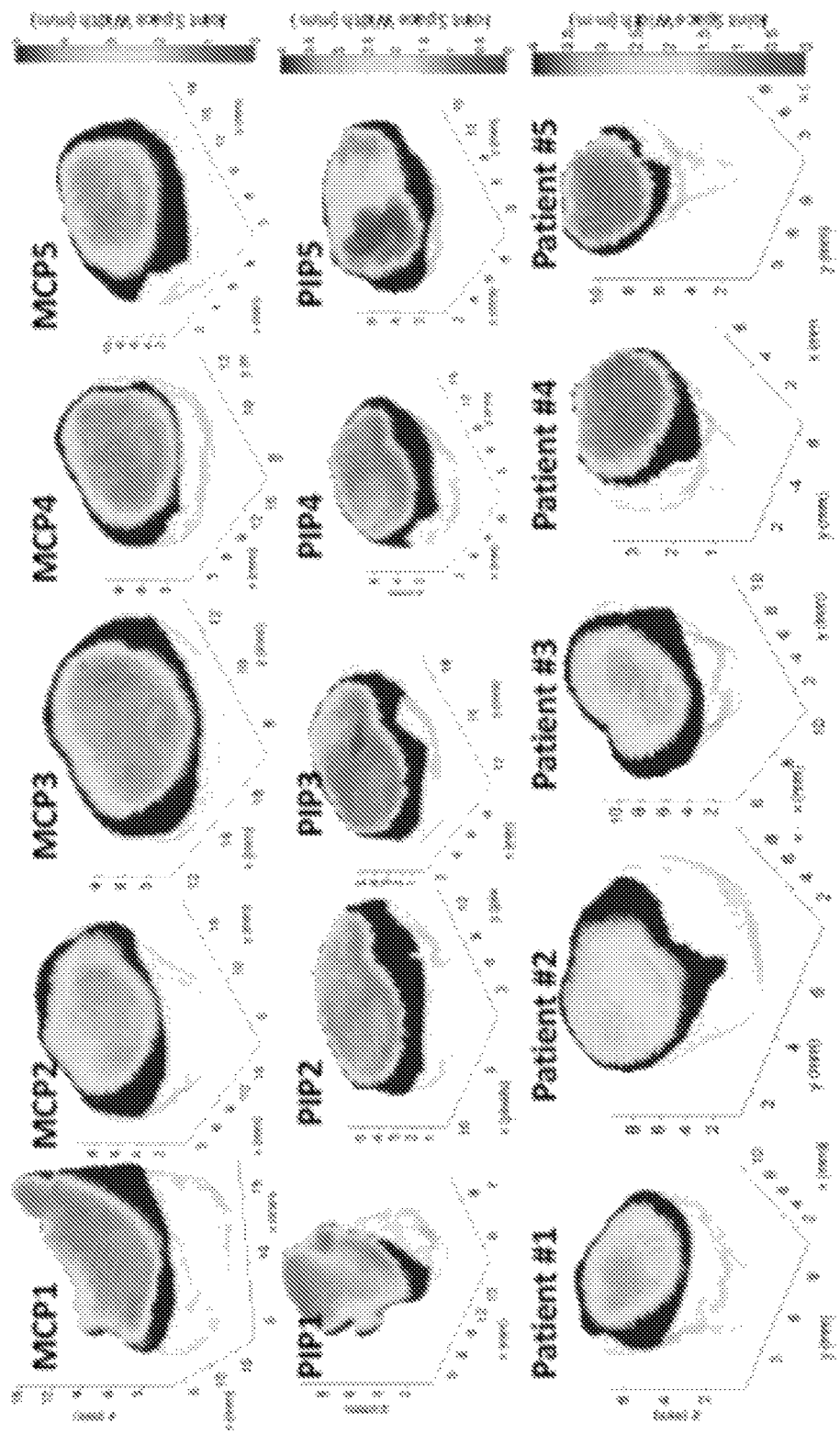
FIG. 16 illustrates joint space maps calculated in the hand, according to an embodiment of the present invention.

Joint space width is a surrogate measure for diagnosis and monitoring of different forms of arthritis, including OA and RA. Typically, Sharp-Larsen scores derived from radiographs are used to measure RA progression in hands and wrists, although such assessment is known to exhibit high inter-reader variability, inability to differentiate overlapping structures, and insensitivity to subtle joint space changes. Similarly, OARSI grading is used for OA, which may exhibit similar variability. Volumetric assessment of cartilage (closely linked with OA) is possible from MRI, although segmentation can be a challenge. In high-resolution CBCT, the opportunity arises for exquisite quantification of 3D joint space in the form of a joint space map as a substitute for underlying cartilage quantification. To overcome inaccuracy and degeneracy associated with conventional measures (e.g., closest point methods or distance along a given axis), a method to characterize joint space that provides a non-degenerate correspondence across the intra-articular space can be used. The technique employs a physics-based model in which bone surfaces are treated as surfaces of a 'capacitor,' and the associated 'field lines' present a unique characterization of the intra-articular space. The distance between proximal and distal surfaces is uniquely computed as the distance along field lines using the Laplacian (where V is the potential and x, y, and z are Cartesian coordinates), yielding a unique, robust, and quantitative assessment of the joint space, since field lines are always orthogonal to the surface, as shown in FIG. 13. Application to CBCT images of the knee (sitting and standing) and hand (various patients and pathologies) are shown in FIGS. 14A-14C and FIGS. 15A-15D. FIG. 16 illustrates exemplary joint space maps calculated in the hand.

The device of the present invention demonstrates accuracy in BMD within ~5% of a clinical standard QCT system based on MDCT. Intra-osseous bone structure morphomertry shows an improvement over MDCT and good correlation with gold standard micro CT. Agreement in most morphometric indices were found to be within 5%, with the exception of DA, which may require further improvement in spatial resolution. Joint space maps calculated using high-resolution CBCT were able to measure and visualize subtle changes in joint space morphology between weight-bearing and non-weight bearing scans that are not possible using conventional whole-body MDCT. Moreover, the preliminary results demonstrated the ability to identify slight anatomical differences in pathologic fractures with reduced and disrupted joint space morphology. Further improvement in the accuracy of pQCT metrics derived from CBCT is currently underway via improved x-ray scatter correction techniques, beam-hardening corrections, system calibration, and novel reconstruction methods, including statistical iterative reconstruction. The ability to perform automatic pQCT analysis in the extremities with each CBCT scan could offer a valuable addition to diagnostic performance and assessment of treatment response in a spectrum of bone and joint diseases, enabling early detection, treatment planning and longitudinal monitoring as well as reduction in cost, workflow, and radiation dose.

Embodiments involving a predefined location and density of the calibration phantoms make it possible to locate the phantoms automatically, analyze histograms and attenuation coefficients (or Hounsfield units/CT number) versus density without need for manual interaction. Quantitative analysis of the image (for example, BMD) or other quantitative information of the desired structures can thereby be derived automatically according to user preferences.

Although much of the description is based on cone-beam CT scanner using flat panel detectors (FPD), the concept is equally applicable to other volumetric imaging devices, including: Helical CT scanners using Multi-row detectors and fan beam geometry; O-arm and C-arm scanners (based on cone-beam geometry and FPDs); Micro CT scanners; and image-guided radiotherapy systems. The phantoms can also be liquid in composition. Cylindrical phantoms are shown here, although phantoms of other shapes and sizes can be incorporated.

The proposed device and associated methods are described herein with respect to bone mineral density (BMD) calculation, bone structure assessment, and joint space analysis. However, other potential applications include measuring calcium content in arteries, assessing density and structures in lungs or other organs, and performing biopsies. Target anatomy need not be confined to human extremities as described in the example preferred embodiment. The concept could be equally useful in performing quantitative imaging on other structures as well as in veterinary imaging. The many features and advantages of the invention are apparent from the detailed specification, and thus, it is intended by the appended claims to cover all such features and advantages of the invention which fall within the spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A device for calibrated cone beam computed tomography (CBCT) scanning, comprising:
    a gantry, said gantry defining a generally cylindrical opening configured for receiving the patient for examination, said gantry also having a wall configured for housing components of the device;
    an X-ray source configured to emit X-rays that penetrate the patient;
    a detector positioned opposite said X-ray source, such that said detector receives the X-rays emitted from the X-ray source, wherein the detector defines a nominal X-ray field of view for the device such that any item in the field of view is imaged by the device; and
    a calibration phantom at least one of attached to or contained within said wall of said gantry, said calibration phantom positioned such that the calibration phantom is imaged by the device.

2. The device of claim 1 wherein the calibration phantom is positioned within the opening configured to receive the patient.

3. The device of claim 1 wherein the calibration phantom is positioned in the interior space defined by the gantry.

4. The device of claim 1 wherein the calibration phantom is positioned on an outer surface of the interior of the gantry.

5. The device of claim 1 further comprising an encasement for the calibration phantom.

6. The device of claim 5 wherein the encasement further comprises a uniform density and wherein said uniform density is not a density of the calibration phantom.

7. The device of claim 1 wherein the calibration phantoms comprise six calibration phantoms.

8. The device of claim 7 wherein the six calibration phantoms are oriented longitudinally in a ring about the generally cylindrical opening of the gantry.

9. The device of claim 1 wherein the calibration phantom is generally cylindrical in shape.

10. The device of claim 1 wherein the calibration phantom is of a predetermined length to cover the entire field of view of the device.

11. The device of claim 1 wherein the calibration phantoms comprise a solid composition.

12. The device of claim 1 wherein the calibration phantoms are positioned entirely within the field of view.

13. The device of claim 1 wherein the calibration phantoms are positioned outside of the field of view.

14. The device of claim 1 wherein the calibration phantom comprises a known Hounsfield unit (HU).

15. The device of claim 1 wherein the calibration phantom comprises a known calcium density.

16. The device of claim 1 wherein the device is further configured for weight bearing imaging.

17. A device for calibrated cone beam computed tomography (CBCT) scanning, comprising:
    a gantry, said gantry defining a generally cylindrical opening configured for receiving the patient for examination, said gantry also having a wall configured for housing components of the device;

an X-ray source configured to emit X-rays that penetrate the patient;

a detector positioned opposite said X-ray source, such that said detector receives the X-rays emitted from the X-ray source, wherein the detector defines a nominal X-ray field of view for the device such that any item in the field of view is imaged by the device; and a calibration phantom positioned at least one of attached to or contained within said wall of said gantry, said calibration phantom positioned around the generally cylindrical opening, such that the calibration phantom is imaged by the device.

18. The device of claim 17 wherein the calibration phantom comprises six calibration phantoms.

19. The device of claim 18 wherein the six calibration phantoms are positioned longitudinally in a ring around the generally cylindrical opening.

20. The device of claim 19 wherein the six calibration phantoms are spaced such that they are all at least partially within the field-of-view.

* * * * *